United States Patent [19]

Fine

[11] 4,200,981
[45] May 6, 1980

[54] DENTAL ARTICULATOR AND TRAY SYSTEM

[76] Inventor: Ronald J. Fine, P.O. Box 2548, Framingham, Mass. 01701

[21] Appl. No.: 836,791

[22] Filed: Sep. 26, 1977

[51] Int. Cl.² ............................................. A61C 11/00
[52] U.S. Cl. ..................................................... 433/60
[58] Field of Search ........................................... 32/32

[56] References Cited

U.S. PATENT DOCUMENTS

| 565,326 | 8/1896 | Bragg | 32/32 |
|---|---|---|---|
| 654,109 | 7/1900 | Backstrom | 32/32 |
| 664,830 | 1/1901 | Bryan | 32/32 |
| 1,711,019 | 4/1929 | Gambill | 32/32 |
| 2,365,475 | 12/1944 | Klein | 32/32 |
| 2,619,725 | 12/1952 | Roeser | 32/32 |
| 3,808,689 | 5/1974 | Spinella | 32/32 |

FOREIGN PATENT DOCUMENTS 117133  7/1918  United Kingdom ........................ 32/32

Primary Examiner—Louis G. Mancene
Assistant Examiner—John J. Wilson

[57] ABSTRACT

A dental articulator comprises a pair of opposed tray mounting arms pivotally connected together and removably securing thereto dental model mounting trays, an abutment on one end of each arm engaging surfaces formed in the tray to prevent lateral and vertical movement of one end of the tray, a key on the tray engaging a keyway in the arm to prevent lateral movement of the other end of the tray and a releasable clamp engaging an angular surface of the tray other end to prevent vertical tray movement. A dental model is adhesively secured to a mounting surface of the tray.

15 Claims, 8 Drawing Figures

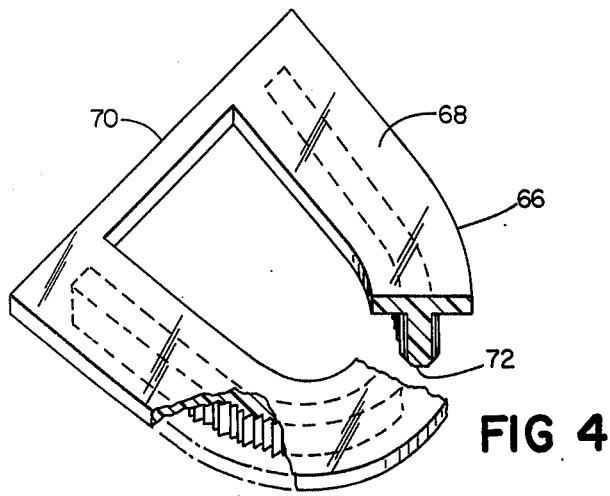
FIG 3
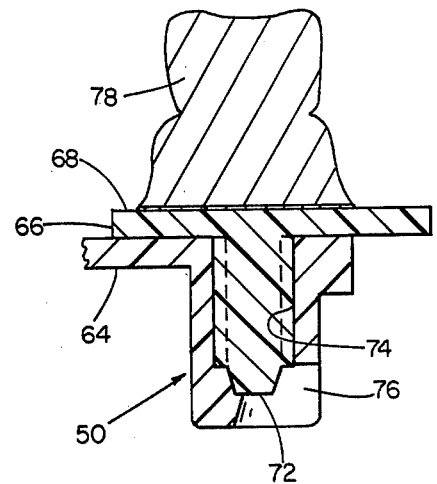
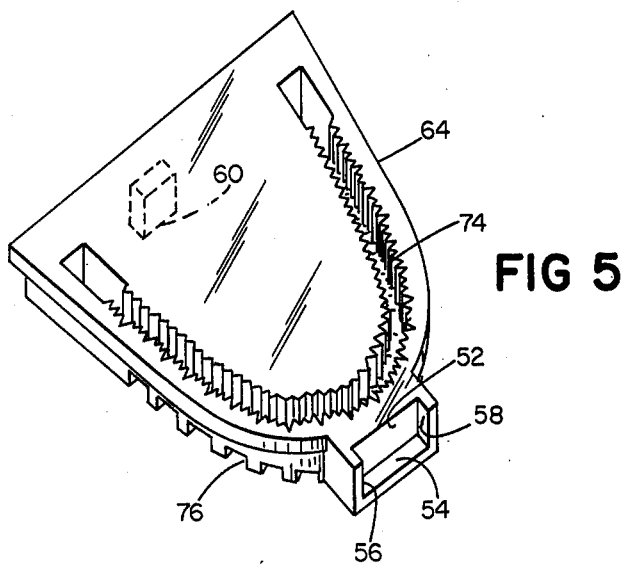
FIG 4
FIG 5
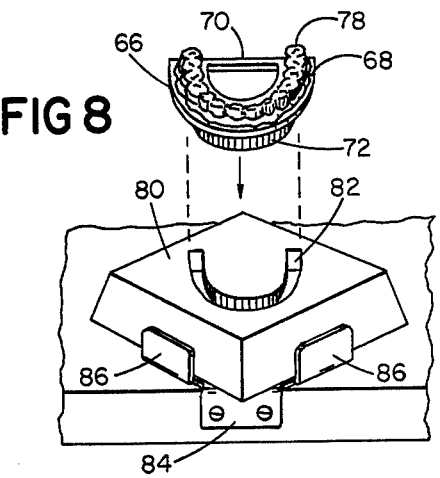
FIG 8
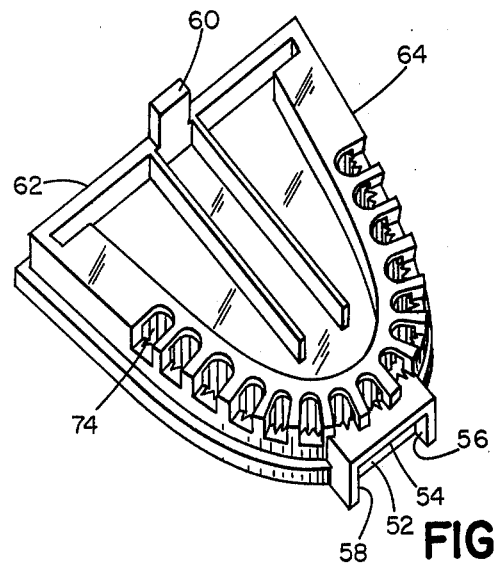
FIG 6
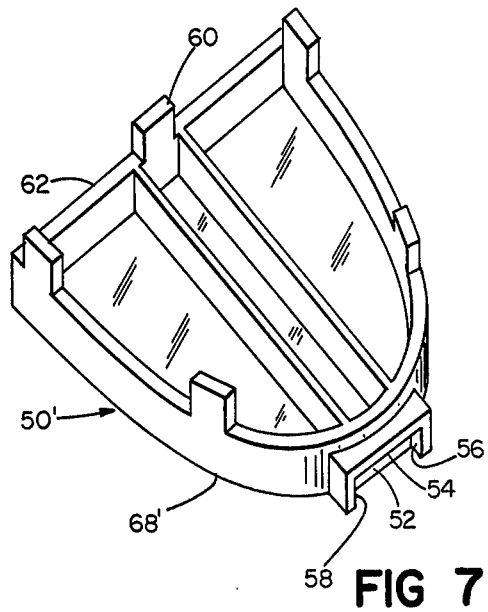
FIG 7

DENTAL ARTICULATOR AND TRAY SYSTEM

This invention relates to a dental model preparation and more particularly to a novel dental articulator and tray system.

It is a principal object of this invention to provide a system which in use will rigidly secure the dental model in position without risk of damaging the model. It is another object of the invention, however, to provide a system from which the model may be released, as desired, yet which may be resecured in its original position. Yet another object is to provide a system which enables storage of models for future reference and which enables reassembly on different identical articulators. Another object is to provide a system which eliminates many time consuming steps normally employed in the preparation of dental models.

In general, the invention features a system comprising the combination of an articulator and preformed dental model mounting means, preferably a tray, in which the tray is mounted on each arm of the articulator and the tray model articulator arms have spaced along the arm cooperating means mutually engaged to prevent vertical lateral and longitudinal movement of the tray, including means for selectively disengaging the tray and the arm. The invention also features separately the articulator and the tray adapted for use together.

In particular embodiments of the invention the articulator comprises an abutment spaced from the arm and projecting a limited distance toward a clamp member. The abutment has side surfaces and a surface facing the arm. The tray is provided with a recess defining surface engageable against the abutment surfaces. Spaced from the abutment is a clamp member for releasably securing the tray. The clamp member has an abutment surface pivotally connected thereto. The tray has an angular surface engageable by the clamp member exerting force components toward both the abutment and the arm. The tray is provided with a key engageable in a keyway in the arm adjacent the clamp member. In one embodiment, the tray comprises a base and a removable upper portion carrying the model mounting surface.

Other objects, features and advantages of this invention will be apparent to those skilled in the art from the following detailed description of a preferred embodiment thereof taken together with the accompanying drawings, in which:

FIG. 3 is an enlarged fragmentary sectional view of a portion of the tray taken along the line 3—3 of FIG. 1;

FIG. 4 is an isometric view, partially broken away, of model mounting portion of the tray illustrated in FIG. 1;

FIG. 5 is an isometric view of base portion of the tray illustrated in FIG. 1;

FIG. 6 is an inverted isometric view of the tray base illustrated in FIG. 5;

FIG. 7 is an inverted isometric view of an alternate one piece mounting tray; and FIG. 8 is a reduced, exploded, isometric view of a cutting block and model mounting portion of the tray.

Figure 1:
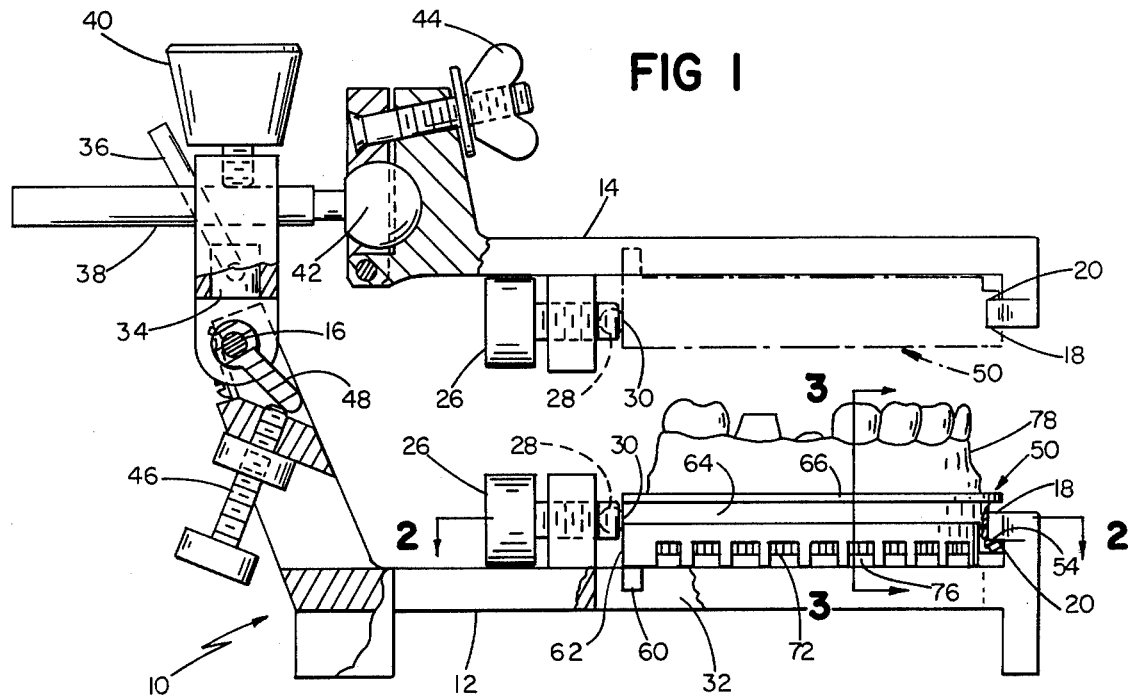
FIG. 1 is a side elevation, partly in section of an articulator having dental model mounting trays secured thereto, one tray being shown only in phantom for clarity of illustration.

The dental articulator and tray system is illustrated in FIG. 1. The articulator 10 comprises a pair of opposed tray mounting arms 12,14 pivotally connected together at pivot 16.

Figure 2:
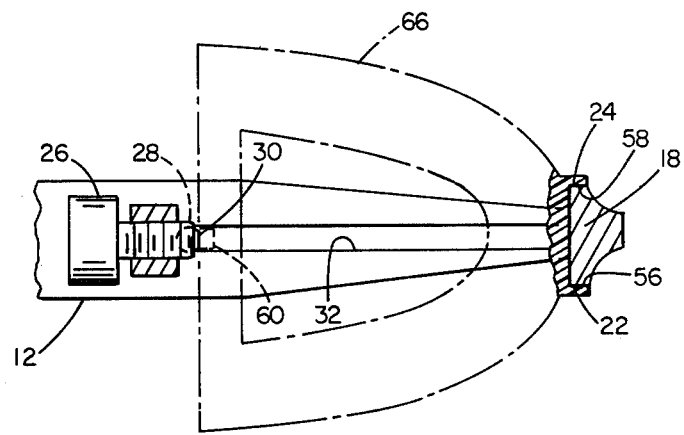
FIG. 2 is a plan view taken along the line 2—2 of a portion of the lower arm of the articulator with the tray shown partially in section and partially in phantom for clarity of illustration.

As illustrated in FIGS. 1 and 2, arms 12,14 are each provided with an integral end abutment 18 which is spaced from the arm to which it is connected, toward the other arm, and which projects a limited distance toward the pivot. The abutment 18 thus provides a projection having a horizontal surface 20 facing the arm to which it is connected and a pair of vertical side surfaces 22,24. Longitudinally spaced from abutments 18 on each arm 12,14 is an adjustable clamp member 26. Pivotally connected to the end of clamp member 26 is a ball 28 having an abutment surface 30 facing abutment 18. A keyway 32 is provided in each arm 12,14 adjacent clamp member 26. In preferred embodiments of the articulator, adjustment means are provided for adjusting the upper arm 14 relative to arm 12 on the articulator base: post 34 permits rotation of the upper arm 14 about a vertical axis, member 36 selectively engaging post 34 to lock the upper arm in a predetermined position; shaft 38 permits longitudinal adjustment of the upper arm 14, member 40 locking the shaft 38 in a selected position; ball joint 42, with clamp 44, permits universal orientation adjustment of the upper arm; and, in addition, threaded member 46, with lever 48 provides an adjustable stop for the pivot 16.

The dental model mounting tray used with articulator may comprise either the two piece tray 50, illustrated in FIG. 1 and shown in greater detail in FIGS. 3-6, or may comprise a one piece tray 50', illustrated in FIG. 7. Trays 50, 50' are each provided at the front edge portion thereof with a recess 52 which presents horizontal surface 54 facing and engaging the arm facing surface 20 of abutment 18 with the tray firmly seated on the articulator arm. The vertical sides 56,58 of recess 52 engage the side surfaces 22,24 of abutment 18. Thus, the front of the tray 50,50' is secured against vertical and lateral movement as well as forward longitudinal movement of the cooperation of abutment 18 and recess 52. The rear edge portion of trays 50,50' is secured against movement laterally by integral key 60 which extends into keyway 32 and engages the sides thereof. The rear surface 62 of trays 50, 50' is formed at a small angle, e.g., 2°, from the vertical and faces away from the arm to which the tray is connected. Abutment surface 30 of clamp member 26, because of its pivoted connection, engages tray surface 62 at an angle facing the arm and exerts a force component directed toward the arm. The abutment surface 30 and tray surface 62 thus, cooperate to secure the rear of tray 50,50' against vertical and longitudinal movement.

As best shown in FIGS. 3-6, the two piece tray 50, generally similar to trays shown in U.S. Pat. Nos. 3,581,398 and 3,838,187, comprises a base 64 and a model mounting portion 66. Mounting portion 66 comprises a flat surface 68, generally arch shaped, the rear portions of which are connected by bridge 70. A continuous male key 72, corrugated on both sides to form a plurality of teeth, extends below mounting surfaces 68. Base 64 a female keyway 74 is corrugated to match and receive key 72. At regular matching intervals, the outer corrugations in key 72 and keyway 74 are preferably enlarged to facilitate matching the mounting portion 66 with the proper position in the base 64 if the former is cut into segments. The outer portion of base 64 is preferably undercut, as at 76, to facilitate removal of the mounting portion 66 or segments thereof. The corrugations of the key 72 and keyway 74 preferably have a slight taper, e.g., 0.5°, for secure fit. In a preferred embodiment the mounting portion is injection molded conventionally from a 30% glass filled nylon. Base 64 in a preferred embodiment is formed of a 30% glass filled styrene and to assure accurate dimensioning of the keyway 74 is injection molded directly around the key 72 of the previously formed mounting portion.

One piece tray 50' in a preferred embodiment is molded of 30% glass filled styrene and has a continuous flat mounting surface 68'.

In use, a dental model 78 is first cast from dental stone in conventional manner. When the model 78 is formed, its base is ground flat and then scored. The mounting portion 66 of a two part tray 50 is then removed from its base 64. The mounting surface 68 of tray 50 or surface 68' of a one piece tray 50', whichever is used, and the base of the model are painted with an accelerator of a two part adhesive system and the model is then secured to the tray mounting surface 68,68' with an adhesive, such as an acrylic adhesive, selected for its void filling and rapid setting qualities, applied to the mounting surface 68. The mounting portion 66 of a two part tray 50 may then be cut with the model 78 into segments as appropriate; bridge 70 is first cut away. In cutting the model and mounting portion 66, the mounting portion 66 is preferably placed in a polystyrene foam block 80 having a recess 82 to firmly receive male key 72, as shown in FIG. 8; the block 80 is then placed against upstanding walls 86 of a sheet metal fixture 84 secured to a work surface and the model and mounting portion are cut through in the block into appropriate segments. The segments may then be reassembled in base 64. Trays 50 or 50' are then assembled on arms 12,14 of articulator 10 as above described, and the upper arm 14 is adjusted as required.

Advantageously, once dental models are adhered to the trays, the trays may be assembled and disassembled at will from the articulator. When assembled to the articulator, the trays are firmly secured in position. The trays and models on reassembly with the articulator are positively located without need for concern about changes in orientation, thus enabling mailing of the trays from, e.g., a dental laboratory to a dentist. The models may also be preserved for future reference. The articulator is not unnecessarily tied up for use with a single set of dental models which are not being worked upon. The two piece tray, with its integral dowel system eliminates multiple steps in preparing the models.

Other embodiments of this invention will be apparent to those skilled in the art which are within the scope of the following claims.

What is claimed is:

1. A dental articulator and tray system in which said articulator comprises a pair of opposed tray mounting arms pivotally connected together and in which preformed dental model mounting trays are secured to said arms, each arm and the mounting tray secured thereto comprising cooperating means mutually engaged at positions spaced longitudinally along said arm adapted to resist lateral, vertical, and longitudinal movement of said tray relative to said arm, characterized in that said cooperating means comprises: an abutment on said arm having vertical side surfaces and a horizontal surface vertically spaced from and facing said arm and vertical side surfaces and a horizontal surface facing away from said arm on said tray respectively engaging said abutment side and horizontal surfaces to prevent lateral and vertical movement of said tray, said side and horizontal surfaces of said abutment and said tray being defined by a projection on one of said abutment and said tray extending into a recess on the other thereof; a clamp member spaced longitudinally along said arm from said abutment and having an abutment surface releasably engaging a surface of said tray with force components directed toward said abutment and said arm to prevent longitudinal and vertical movement of said tray; and, adjacent said clamp member, mutually engageable means on said articulator and said tray to prevent lateral movement of said tray.

2. The system claimed in claim 1 in which said clamp abutment surface engages an angular surface of said tray for exerting said force components toward said abutment and toward said arm.

3. The system claimed in claim 2 in which said abutment surface on said clamp member is pivotally connected to said clamp member.

4. The system claimed in claim 1 in which said means adjacent said clamp preventing lateral movement of said tray comprises a key on said tray in a keyway in said arm.

5. The system claimed in claim 1 in which said projection is on said abutment and projects a limited distance toward said clamp member and in which said abutment projects into said recess formed in said tray.

6. The system claimed in claim 5 in which said means adjacent said clamp preventing lateral movement of said tray comprises a key on said tray in a keyway in said arm.

7. The system claimed in claim 6 in which clamp abutment surface is pivotally connected to said clamp member and engages an angular surface of said tray for exerting said force components toward said abutment and said arm.

8. A dental articulator adapted to releasably secure preformed dental model mounting trays thereto, the articulator comprising a pair of opposed tray mounting arms pivotally connected together and means for securing the trays to the arms, characterized in that the means on each arm for securing a tray comprises: an abutment having vertical side surfaces and a horizontal surface vertically spaced from and facing the arm, said abutment surfaces adapted to engage opposed matching surfaces on said tray to prevent lateral movement of the tray and vertical movement thereof away from the arm, said vertical and horizontal surfaces of said abutment defined by a projection on or a recess in said abutment; a releasable clamp member spaced longitudinally along said arm from said abutment, said clamp member having an abutment surface adapted to engage a surface of said tray at an angle directed toward said arm with force components directed toward said abutment and said arm to prevent vertical movement of said tray away from said arm and, with said abutment, to releasably secure said tray against longitudinal movement; and means adjacent said clamp member adapted to engage cooperating means on said tray to prevent lateral movement of said tray.

9. The articulator claimed in claim 8 in which said abutment comprises a projection spaced vertically from said arm and extending a limited distance toward said clamp member, said horizontal surface facing said arm.

10. The articulator claimed in claim 8 in which said clamp member abutment surface is pivotally connected to said clamp member.

11. The articulator claimed in claim 8 in which said means adjacent said clamp member comprises a keyway in said arm adapted to receive a key on said tray.

12. A preformed dental model mounting tray adapted to be releasably secured to a dental articulator, said tray having a top, a bottom and front and rear edge portions extending between said top and said bottom, a dental model mounting surface being provided on the top thereof, characterized in that said tray comprises: means on one of said edge portions adapted to engage an abutment on said articulator, said means comprising vertical side surfaces and a horizontal surface facing upwardly in the direction of said tray top spaced from said bottom adapted to engage opposed matching surfaces on said articulator to prevent lateral and vertical movement of the tray, said vertical and horizontal surfaces of said tray defined by a recess in or a projection on said tray; a surface of an other said edge portion, opposite said one edge portion, extending at an angle to the vertical, said surface extending from said other edge at an angle generally toward said one edge portion, adapted for engagement by a clamp member spaced from said abutment to transmit force components downwardly away from said tray top and parallel to said tray top toward said one edge portion; and means adjacent said angled surface adapted to engage cooperating means on said articulator to prevent lateral movement of said tray.

13. The tray claimed in claim 12 in which said side surfaces and said horizontal surface are surfaces of an abutment receiving recess in said tray.

14. The tray claimed in claim 12 in which said means adjacent said angled surface comprises a key formed in the bottom of said tray adapted to engage a keyway in said articulator.

15. The tray claimed in claim 14 in which said tray comprises two parts, a base and a top removable from said base, said model mounting surface being positioned on said top and said front and rear edge portions and said key being formed in said bottom.

* * * * *